United States Patent [19]

Kordes et al.

[11] Patent Number: Plant 6,117

[45] Date of Patent: Mar. 1, 1988

[54] ROSE PLANT KORHOLST

[75] Inventors: Reimer Kordes; Werner Kordes; Hermann Kordes, all of Klein Offenseth-Sparrieshoop, Fed. Rep. of Germany

[73] Assignee: Jackson & Perkins Company, Medford, Oreg.

[21] Appl. No.: 833,614

[22] Filed: Feb. 27, 1986

[51] Int. Cl.[4] ..... A01H 5/00

[52] U.S. Cl. ..... Plt./1

[58] Field of Search ..... Plt. 1, 28–29

*Primary Examiner*—Robert E. Bagwill

*Attorney, Agent, or Firm*—Manford R. Haxton

[57] ABSTRACT

A shrub rose variety having dark green foliage and bright red flowers borne on an upright vigorous growing shrub that has good mildew resistance in Southern California.

1 Drawing Figure

This present invention relates to a new and distinct variety of rose plant of the shrub class which was originated by crossing the varieties, Tornado and Sämling, unpatented, with the variety, Chorus, unpatented.

The primary objective of this breeding was to produce a new rose variety of the shrub class exhibiting profuse flowering upright growth habit and red colored flowers. This objective was substantially achieved along with other desirable improvements as evidenced by the following unique combination of characteristics which are outstanding in the new variety and which distinguish it from its parents as well as from all other varieties of which I am aware:

1. Dense vigorous, upright growth habit;
2. Free blooming;
3. Dark red flower color;
4. Dark green, glossy foliage;
5. Low petal count (10–14); and
6. Mildew resistance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Tornado and Samling, unpatended.

*Pollen parent.*—Chorus, unpatented.

Classification:

*Botanical.*—Rosa hybrid.

*Commercial.*—Shrub.

FLOWER

Observations made from specimens grown in a greenhouse at Irvine, Calif. in July–September, 1985.

Blooming habit: Continuous.

Bud:

*Size.*—1" when petals start to unfurl.

*Form.*—Short, blunt top.

*Color.*—When sepals first divide, very dark red — darker than Red Group 46A; when half blown, upper side of petals Dark Red; varies between 45A and B and 46A and B; lower side of petals Dark Red, varies between 45A and B and 46A and B.

*Sepals.*—Color: Green (Green Group 143A) tinged with red (Red Group 45A). Three appendaged sepals lightly appendaged. Two unappendaged sepals hairy edge.

*Receptacle.*—Color: Green (Group 143A. Shape: Funnel. Size: Small. Surface: Very few, fine hairs.

*Peduncle.*—Length: Short. Surface: Glandular. Color: Medium Green and bronzy. Strength: Stiff.

Open bloom:

*Size.*—Medium. Average open size 2½–3".

*Borne.*—Several together, in clusters, flat.

*Stems.*—Short, strong.

*Form.*—When first open, high center. Permanence: Flattens and undulates.

*Petalage.*—Number of petals under normal conditions: 10–15.

*Color.*—Center of flower: Upper side of petals, Red Group, varies between 45A to B and 46A to B; reverse side of petals, Red Group, varies between 45A to B and 46A to B. Base of petals, small white area. Major color: Red Group 45A to B.

*Variegations.*—Occasional white streak.

*Discoloration.*—General tonality at end of first day: None. Third day: Slight fading.

*Fragrance.*—Slight.

Petals:

*Texture.*—Thick.

*Shape.*—Roud, notched.

*Form.*—Flat with tips, slightly recurved.

*Arrangement.*—Imbricated, Petaloids in center.

*Persistence.*—Drop off cleanly.

*Lastingness.*—On the plant, long.

Reproductive parts:

*Anthers.*—Medium, many. Color: Yellow, Arrangement: Regular around styles.

*Filaments.*—Color: White.

*Pollen.*—Lemon yellow.

*Styles.*—Color: White.

*Stigmas.*—Color: White.

PLANT

Form: Upright shrub.
Growth: Vigorous and dense.
Foliage: Number of leaflets on normal mid-stem leaves: 5–7.
*Size.*—Medium.
*Quantity.*—Normal.
*Color.*—New foliage: Bronze colored. Old foliage: Green Group 138A.
Leaflets:
*Shape.*—Oval pointed.
*Texture.*—Smooth.
*Edge.*—Serrated.
*Serration.*—Mostly single, small.
*Petiole.*—Rachis: Color: Green with red ribs. Underside: With prickles.
*Stipules.*—Medium, bearded.

*Disease resistance.*—Resistant to mildew, under normal growing conditions at Irvine, Calif.
Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Medium, hooked slightly downward.
*Color when young.*—Red.
Small prickles:
*Quantity.*—On main stalks, none. On laterals, none.

We claim:

1. A new and distinct variety of rose plant of the shrub class, substantially as herein shown and described, characterized particularly as to novelty by the unique combination of dark green foliage and bright red flowers borne on an upright vigorous growing shrub that has good mildew resistance in Southern California.

* * * * *

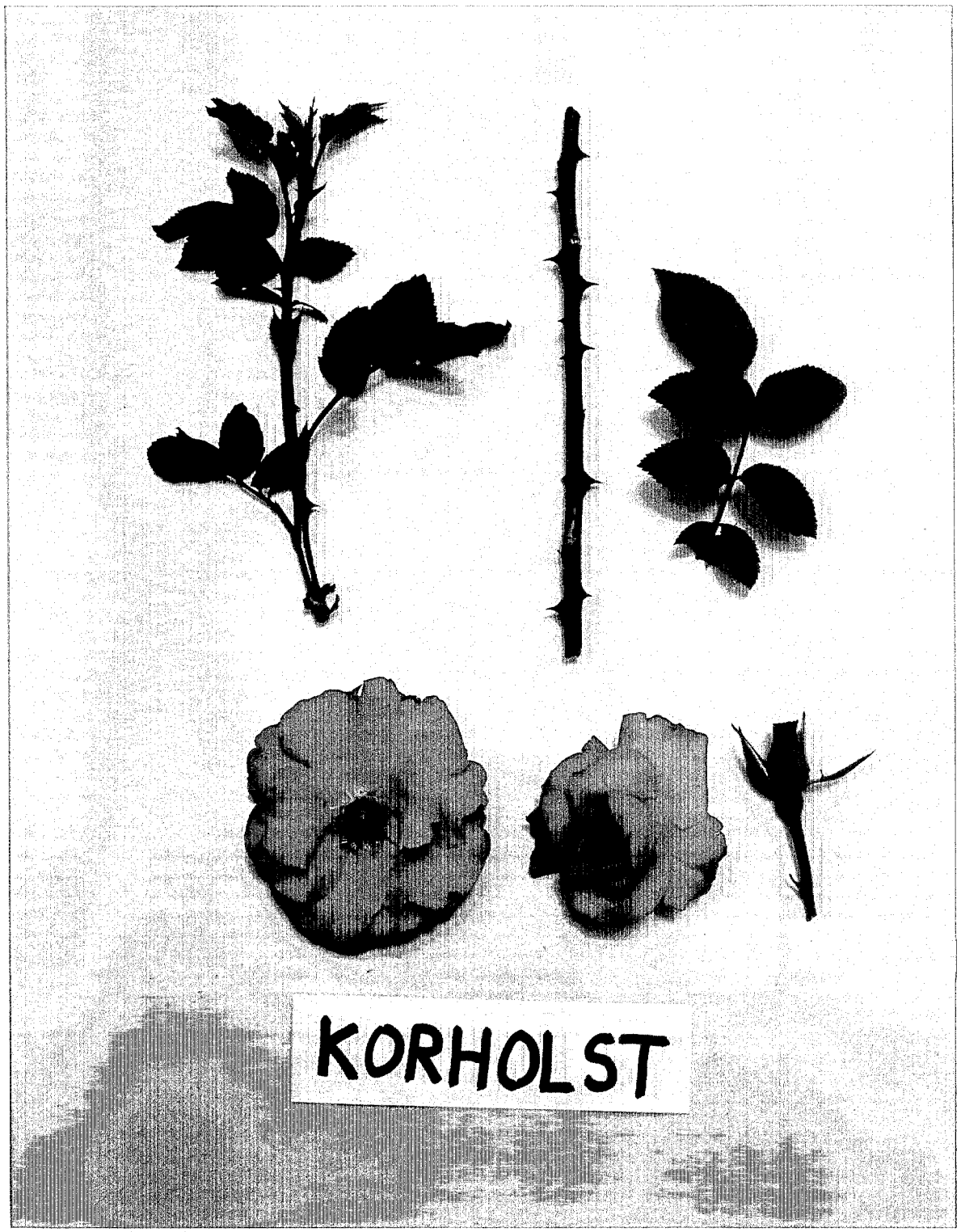
KORHOLST